US00PP25899P3

(12) United States Plant Patent
Probasco et al.

(10) Patent No.: US PP25,899 P3
(45) Date of Patent: Sep. 15, 2015

(54) HOP PLANT NAMED 'HBC 366'

(50) Latin Name: *Humulus lupulus*
Varietal Denomination: HBC 366

(75) Inventors: Eugene G. Probasco, Yakima, WA (US); Jason Perrault, Selah, WA (US)

(73) Assignee: Hop Breeding Company, LLC., Yakima, WA (US)

( * ) Notice: Subject to any disclaimer, the term of this patent is extended or adjusted under 35 U.S.C. 154(b) by 0 days.

(21) Appl. No.: 13/374,223

(22) Filed: Dec. 15, 2011

(65) Prior Publication Data

US 2012/0167263 P1 Jun. 28, 2012

Related U.S. Application Data

(60) Provisional application No. 61/460,198, filed on Dec. 27, 2010.

(51) Int. Cl.
*A01H 5/00* (2006.01)
*A01H 5/08* (2006.01)

(52) U.S. Cl.
USPC ..... Plt./236
CPC ..... *A01H 5/08* (2013.01)

(58) Field of Classification Search
USPC ..... Plt./236
See application file for complete search history.

*Primary Examiner* — Susan McCormick Ewoldt
(74) *Attorney, Agent, or Firm* — Ballew Law

(57) ABSTRACT

A new hop plant named 'HBC 366' is disclosed. The cones of 'HBC 366' mature in late September, and yield a crop of 2200 to 2700 pounds per acre. 'HBC 366' is used for its unique aromatic quality, high alpha acid content and exceptional yield.

4 Drawing Sheets

Genus and species: *Humulus lupulus.*
Variety denomination: HBC 366.

STATEMENT REGARDING FEDERALLY SPONSORED RESEARCH OR DEVELOPMENT

None

BACKGROUND OF THE INVENTION

'HBC 366' is a product of a controlled breeding program carried out by the inventors in the Yakima Valley of Washington state. 'HBC 366' was one of several seedlings resulting from a cross made in 2001 of female parent 'YCR-5' (patented as "YCR Accession No. 5" U.S. Plant Pat. No. 12,404) and male parent 'YCR 136' (not patented). A single plant of 'HBC 366' was selected in 2003, and in 2007 was expanded to 70 plants, which were planted in the area of Toppenish, Wash. The plants were observed and evaluated for several years, and in 2009 were expanded for further observation and evaluation in the Toppenish, Wash. area. A three acre test plot of 'HBC 366' was established in 2009. Throughout several generations of asexual propagation, 'HBC 366' has been observed to retain its distinctive characteristics and remain true to type. HBC 366 is distinguished from other known hop cultivars by its high total oils, its heavy solid cones with large amounts of lupulin, and by the unusual yellow color (Yellow green 154C) of its immature leaves during the spring—a leaf characteristic similar to the Comet hop variety. HBC 366 has a distinctive citrus aromatic property.

HBC 366 is distinguishable from its parent plants (YCR-5 and YCR 136). HBC 366 is distinguishable from its male parent YCR-136 with flowers that develop into mature hop cones without producing pollen, while flowers of YCR 136 produce pollen without developing into mature hop cones.

TABLE 1 sets forth some of the distinguishing characteristics of HBC 366 as compared to its female parent YCR-5:

| | HBC 366 | YCR-5 |
|---|---|---|
| Alpha Acids % | 14.0% to 17.0% | 15.0% to 17.0% |
| Beta Acids % | 4.0% to 5.0% | 4.5% to 5.5% |
| Cohumulone % | 35.0% to 38.0% | 24.0% to −26.0% |
| Total oils | 2.4 to 2.7 mL/100 g cones | 1.0 to 2.0 mL/100 g cones |

BRIEF DESCRIPTION OF THE PHOTOGRAPHS

Figure 1:
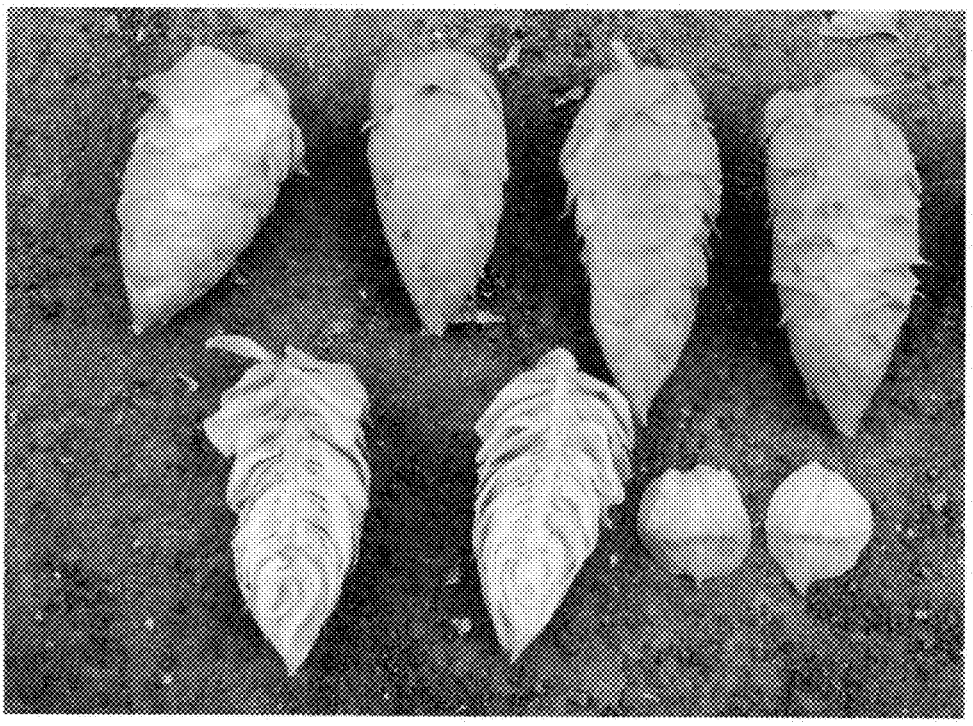
FIG. 1 illustrates whole cones and cross sections of cones of the 'HBC 366' hop plant.
Figure 2:
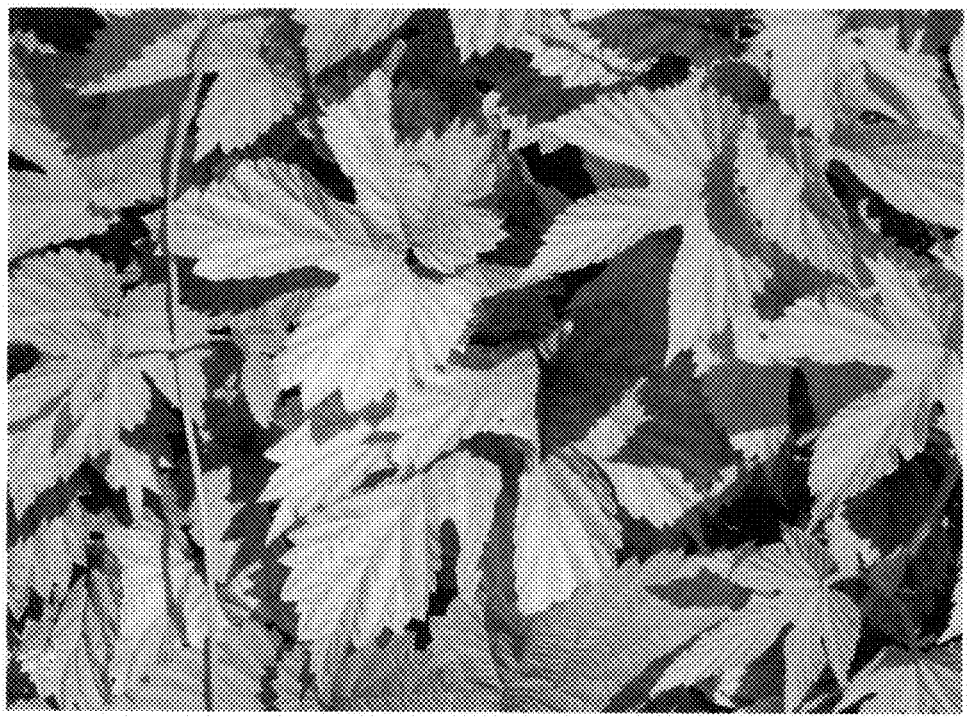
FIG. 2 illustrates the leaves of the 'HBC 366' hop plant.
Figure 3:
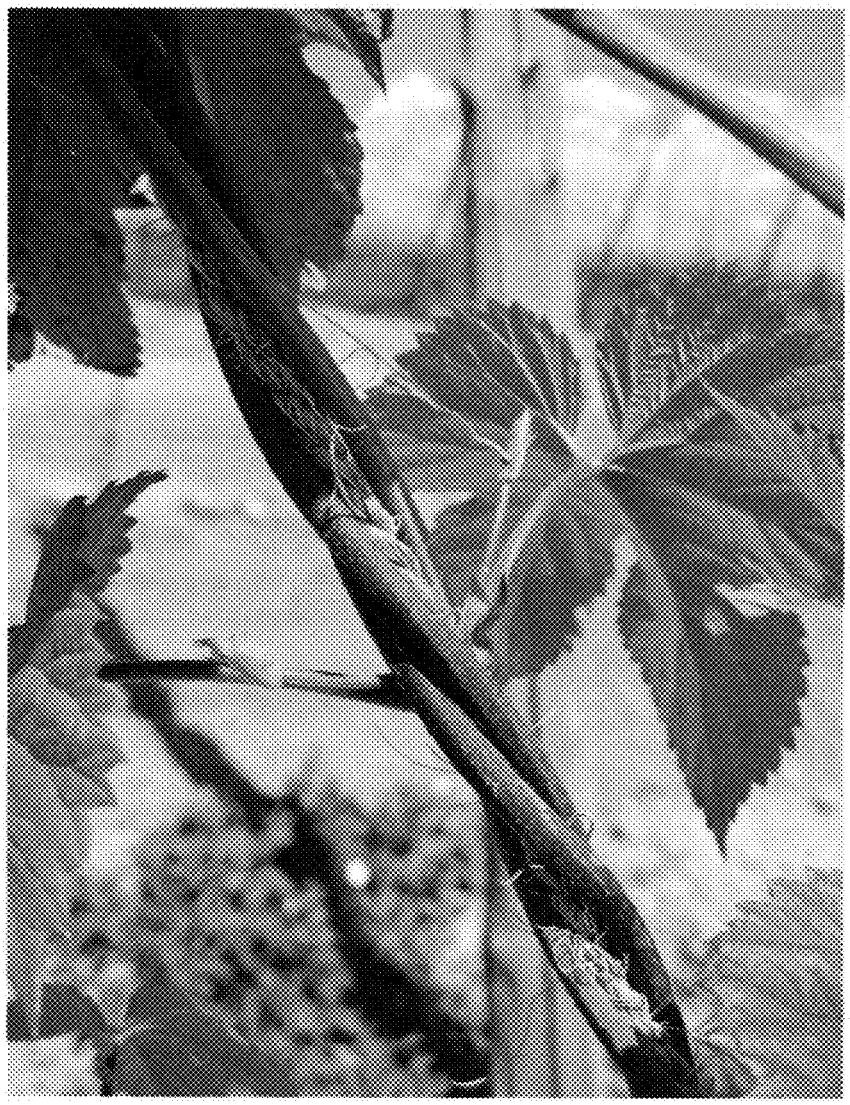
FIG. 3 illustrates the bine and leaves of the 'HBC 366' hop plant.
Figure 4:
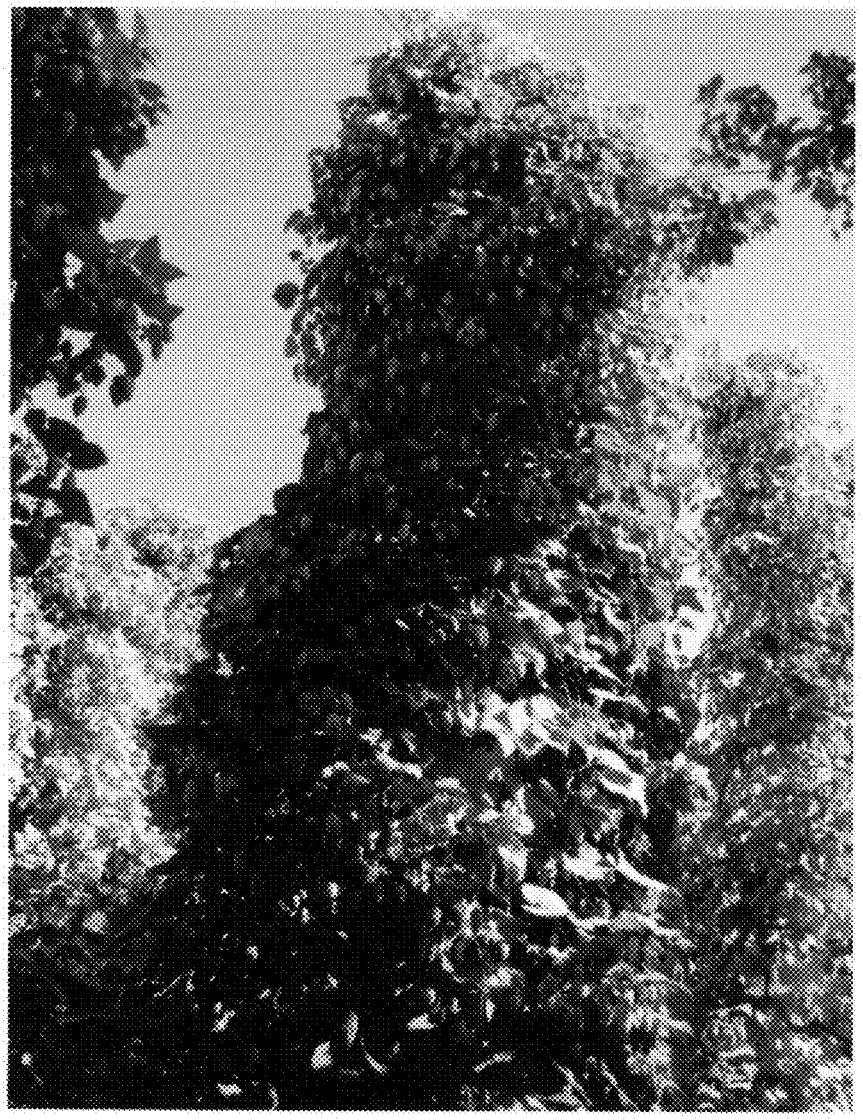
FIG. 4 illustrates a mature 'HBC 366' hop plant grown on a trellis.

The colors of these illustrations may vary with lighting conditions and, therefore, color characteristics of this new variety should be determined with reference to the observations described herein, rather than from these illustrations alone.

DETAILED BOTANICAL DESCRIPTION

The following description is based on observations made during the 2011 growing season at Toppenish, Wash. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant or any group of plants, of the new variety may vary from the stated average.

Species: *Humulus lupulus*.
Ploidy: Diploid.
Use: Brewing.
Disease susceptibility: 'HBC 366' is not resistant to hop downy mildew. 'HBC 366' is moderately resistant to powdery mildew.
Pest susceptibility: 'HBC 366' is not resistant to normal infestations of hop aphid and two-spotted spider mite.
Harvest date: September 12-22 (2011 growing season, Toppenish, Wash.).
Crop yield: 2600 pounds per acre.
Bine:
- *Color.*—Yellow green 146D.
- *Stipule direction.*—Up-forked.
- *Stipule color.*—Yellow green 146D.
- *Bine diameter.*—9.0 mm at base; 8.3 mm at 9 feet; 7.5 mm at 18 feet.

Leaf:
- *Arrangement.*—Opposite.
- *Shape.*—Cordate — Palmate.
- *Average length of mature leaf.*—15.55 cm.
- *Average width of mature leaf.*—15.3 cm.
- *Color of mature leaf upper surface.*—Yellow green 146A-147A.
- *Color of mature leaf lower surface.*—Yellow green 147B.
- *Color of immature leaf upper surface.*—Yellow green 154C.
- *Number of lobes.*—1-7.
- *Margin.*—Serrate.
- *Serrations per inch.*—4-5.
- *Average petiole length* (*mature*).—7.5 cm.
- *Petiole color at base.*—Yellow green 146D.
- *Vein color.*—Yellow green 146D.

Cone:
- *Average weight.*—1030 mg.
- *Average length.*—3.8 cm.
- *Average diameter.*—1.8 cm.
- *Bract tip color.*—Yellow green 144A.
- *Bract base color.*—Yellow green 149D.
- *Bracteole color.*—Yellow green 149D.
- *Cone shape.*—Ovoid.
- *Bract shape.*—Ovate.
- *Bract tip shape.*—Cuspidate.
- *Bract tip position.*—Slightly flared.
- *Bracteole shape.*—Ovate.
- *Pickability.*—Good.
- *Cone storage.*—30% loss of soft resins after 6 month storage at room temperature.

Qualitative analysis:
- *Alpha acids* (*as % of cone weight*).—14.0% to 17.0%.
- *Beta acids* (*as % of cone weight*).—4.0% to 5.0%.
- *Cohumulone* (*as % of alpha acids*).—35.0% to 38.0%.
- *Myrcene* (*as % of total oils*).—31.0% to 34.0%.
- *Humulene* (*as % of total oils*).—18.0% to 20.0%.
- *Caryophyllene* (*as % of total oils*).—11.0% to 14%.
- *Total oils.*—2.4 to 2.7 ml per 100 g cones.
- *Storageability.*—60% to 65% alpha acids remaining after 6 months storage at room temperature.

The invention claimed is:

1. What is claimed is a new and distinct hop plant as shown and described herein.

* * * * *